United States Patent [19]

Rosencwaig et al.

[11] Patent Number: 4,679,946
[45] Date of Patent: * Jul. 14, 1987

[54] EVALUATING BOTH THICKNESS AND COMPOSITIONAL VARIABLES IN A THIN FILM SAMPLE

[75] Inventors: Allan Rosencwaig, Danville; Jon Opsal, Livermore, both of Calif.

[73] Assignee: Therma-Wave, Inc., Fremont, Calif.

[ * ] Notice: The portion of the term of this patent subsequent to Apr. 1, 2003 has been disclaimed.

[21] Appl. No.: 612,077

[22] Filed: May 21, 1984

[51] Int. Cl.$^4$ .................... G01N 21/41; G01N 25/00
[52] U.S. Cl. ........................ 374/5; 356/445; 374/7; 374/57
[58] Field of Search ............... 374/5, 4, 7, 17; 356/237

[56] References Cited

U.S. PATENT DOCUMENTS

| | | | |
|---|---|---|---|
| 3,222,917 | 12/1965 | Roth | 374/5 |
| 3,462,602 | 8/1969 | Apple | 250/338 |
| 3,504,524 | 4/1970 | Maley | 374/5 |
| 3,978,713 | 9/1976 | Penny | 73/643 X |
| 4,243,327 | 1/1981 | Frosch et al. | 374/43 X |
| 4,255,971 | 3/1981 | Rosencwaig | 374/117 X |
| 4,443,106 | 4/1984 | Yasuda et al. | 73/150 R X |
| 4,468,136 | 8/1984 | Murphy et al. | 374/17 X |
| 4,513,384 | 4/1985 | Rosencwaig | 374/7 |
| 4,521,118 | 6/1985 | Rosencwaig | 356/43 X |
| 4,522,510 | 6/1985 | Rosencwaig et al. | 374/7 |
| 4,579,463 | 4/1986 | Rosencwaig et al. | 374/5 X |

OTHER PUBLICATIONS

"Non Contact Optical Position Sensing Using Silicon Photodetectors", William Light, Apr. 1982.
"Non-Destructive Interferometric Detection of Unbonded Layers", P. Cielo, pp. 231-248, Reprint of Optics & Lasers in Engineering-1/14/84.
"Thermal Wave Depth Profiling: Theory", J Opsal & A Rosencwaig, Journal of Applied Physics, Jun. 1982.
"Thermal Wave Detection & Thin-Film Thickness Measurements with Laser Beam Detection", Opsal et al, Applied Optics, 10/15/83, vol. 22, No. 20, pp. 3169-3176.

*Primary Examiner*—Daniel M. Yasich
*Attorney, Agent, or Firm*—Limbach, Limbach & Sutton

[57] ABSTRACT

The subject invention discloses a method and apparatus for evaluating both the thickness and compositional variables in a layered or thin film sample. Two independent detection systems are provided for measuring thermal waves generated in a sample by a periodic, localized heating. One detection system is of the type that generates output signals that are primarily a function of the surface temperature of the sample. The other detection system generates signals that are primarily a function of the integral of the temperature beneath the sample surface. The two independent thermal wave measurements permit analysis of both thickness and compositional variables. An apparatus is disclosed wherein both detection systems can be implemented efficiently within one apparatus.

17 Claims, 4 Drawing Figures

EVALUATING BOTH THICKNESS AND COMPOSITIONAL VARIABLES IN A THIN FILM SAMPLE

TECHNICAL FIELD

The subject invention relates to a new and improved method and apparatus for evaluating both thickness and compositional variables of a layered or thin film sample. A complete analysis of the sample is carried out by measuring thermal waves through two independent detection techniques. The subject invention is particularly suited for analysis common in integrated circuit fabrication. For example, the system is capable of analyzing for both thickness and material composition of thin film layers.

BACKGROUND OF THE INVENTION

There has been considerable effort expended in developing tools for analyzing materials. This interest is particularly strong in the integrated circuit industry. In the latter field, there is a need to develop analytical tools which are capable of nondestructively evaluating thickness and compositional variables of thin films with an extreme degree of accuracy. As can be appreciated, knowledge of a film's electric or dielectric properties and its thickness aids in the design and manufacture of highly sophisticated electronic components.

The composition of a material directly effects its ability to transport energy. There are two primary modes of energy transport, namely, electrical and thermal conductance. In metals, electrical and thermal conductivities are directly related because free electrons are the primary mechanism for the transport of both electrical current and thermal energy. This relationship is defined by the Weidemann-Franz-Lorentz model. Thus, at least for metals, if characteristics of one energy transport system is measured, information about the other energy transport system can be mathematically derived. Once the electrical or thermal conductivities are derived, it is possible to obtain data relating to the material's composition or stoichiometry. For dielectric films there is no relationship between electrical and thermal conductivities. Nevertheless, the thermal conductivity will provide information about the composition or stoichiometry of the dielectric material.

Analysis of metallic materials through the electrical transport system is fairly well developed. Typically, the analytical tools are designed to measure resistivity which is related, in an inverse manner, to electrical conductivity. Referring to FIG. 1, there is illustrated a common analytical tool for evaluating a sample based on resistivity. More specifically, a sample 2 is shown connected to a device known as a four-point probe 4. The four-point probe includes two voltage probes 5 and 6 which are placed in contact with the surface of the thin film layer 3 of the sample. A voltage is placed across the probes through a power source 7. A second pair of probes 8 and 9 are placed in contact with the layer 3 of the sample between the voltage probes 5 and 6. Probes 8 and 9 are connected to a meter 10 for measuring the current passing therebetween.

Note that in the drawing, the layer thickness is substantially exaggerated. In practice, the layer thickness will be significantly less than the spacing between probes 8 and 9. In this situation, it is assumed that the current passes through the entire surface layer 3 of the sample.

In the illustrated apparatus, meter 10 is designed to measure resistivity. Because the current is passing through the whole layer, the resistivity measured is equivalent to the sheet resistance $R_s$ the layer. Unfortunately, sheet resistance does not give unambiguous information concerning the specific characteristics of the material since it is also dependent on layer thickness. In contrast, to find out quantitative information about a particular metallic film's composition or stoichiometry, it is necessary to know its bulk resistivity, rather than its sheet resistance.

Bulk resistivity is related to sheet resistance by the following equation:

$$R_s = \rho/t \qquad (1)$$

where $\rho$ is the bulk resistivity and t is the thickness of the thin film or layer. As can be seen by equation (1), if the sheet resistance is measured, and the thickness is known, the bulk resistivity (and thus the electrical conductivity and material composition) can be readily calculated.

In some manufacturing situations the thickness of the layer of interest is not accurately known. This often occurs in deposition processes used in microelectronic manufacturing techniques. Often times, the composition or stoichiometry of the layer of interest is known such that its bulk resistivity can be inferred. In this case (and referring to equation (1)), if the sheet resistance of the layer can be measured, the thickness (t) of the layer can then be calculated.

From equation (1) and the foregoing discussion, it should be apparent that if the sheet resistance ($R_s$) can be measured, and one of the two remaining parameters, namely, thickness (t) or bulk resistivity ($\rho$) is known, the remaining parameter can be determined. However, if neither the thickness of the layer or its bulk resistivity are known, there is presently no way of deriving either parameter independently from a measurement of only the sheet resistance. The latter situation is unfortunately quite common. For example, in some deposition techniques, an uneven layer will be deposited on a substrate. In addition, because the composition of the deposited material is not constant, the bulk resistivity at any given location is also unknown.

A similar situation is encountered in the analysis of dielectric films. Almost all measurements on such films, such as optical measurements, provide information that is also a function of both film thickness and film composition. Thus, it is not generally possible to obtain independent information on either the film thickness or the film composition from such measurements.

Layer thickness or compositional variables of both metals and dielectrics can also be analyzed through an evaluation of the thermal parameters of the material. Recently, there has been much effort devoted to developing systems for analyzing the thermal characteristics of a sample through the detection of thermal waves.

In a thermal wave detection system, an intensity modulated heating source is focused and scanned across the surface of the sample. As the beam scans across the sample, energy is absorbed by the sample at or near its surface and a periodic surface heating occurs at the modulation frequency of the heat source. This periodic surface heating is the source of thermal waves that propagate from the heated region. The thermal waves interact with thermal boundaries and barriers in a manner that is mathematically equivalent to scattering and reflection of conventional propagating waves. Thus, any features on or beneath the surface of the sample that have thermal characteristics different from their surroundings will reflect and scatter thermal waves and thus become visible to these thermal waves. Thermal waves, however, are critically damped and travel only about one thermal wavelength, thereby having a limited penetration range. In addition, due to their short length of travel, thermal waves themselves are difficult to detect. In addition, in order to detect micron size features in the sample, or to make measurements on very thin films, modulation frequencies on the order of 0.1–20 MHz are often utilized. Detection of such high frequency signals adds complexity to the detection equipment. Nevertheless, a number of systems have been developed for detecting the thermal waves.

One such detection system is disclosed in U.S. Pat. No. 4,255,971, issued Mar. 17, 1981 assigned to the same assignee as the subject invention and incorporated herein by reference. The latter patent discloses a detection technique which is based on the measurement of acoustic waves and is called thermoacoustic microscopy. When the thermal waves have been generated in a sample, a portion of their energy is always transmitted to an acoustic wave at the same frequency because of local stress and strains set up by the thermal waves. The acoustic waves are propagating waves, with much longer wavelengths than the thermal waves. They travel through condensed media with ease and are readily detected with a suitable acoustic transducer placed in acoustic contact with the sample. The magnitude and phase of the acoustic waves are directly related to the interactions undergone by the thermal waves. The magnitude or phase is then measured with suitable phase-sensitive frequency-locked electronics and recorded as a function of the position of the heating source.

As can be appreciated, the above described system, utilizing a piezoelectrical crystal attached to the sample, is a "contact" measurement technique. The latter requirement is time-consuming and potentially contaminating, and is therefore not suitable for production situations encountered in the microelectronics field. Accordingly, there has been significant work carried out in developing noncontact detection techniques. One such noncontact detection technique is described in copending applications, Ser. No. 401,511, filed July 26, 1982 and now U.S. Pat. No. 4,521,118, issued June 4, 1985; and Ser. No. 481,275, filed Apr. 1, 1983 and now U.S. Pat. No. 4,522,510, issued June 11, 1985, and incorporated by reference.

The latter applications describe a method and apparatus for detecting thermal waves by monitoring the local angular changes occurring at the surface of the sample. More specifically, when thermal waves are generated in a localized region of the sample, the surface of the sample undergoes periodic angular changes within the periodically heated area because of local thermoelastic effects. These angular changes occur at a frequency equal to the frequency of the modulated heating.

To monitor these changes, a beam of energy, such as a laser beam, is focused on the surface of the sample at a distance from the center of the heated region in a manner such that it is reflected from the sample surface. Because of the local angular changes occurring at the surface of the sample, the reflected beam will experience angular displacements in a periodic fashion. By measuring the angular displacements, information about the thermal wave activity in the sample can be determined. The latter technique has proved to be a highly sensitive process for detecting thermal waves.

An analysis of the thermal waves present in a sample can be used to derive information regarding either the thickness of thin film layers or their thermal characteristics. A complete discussion of the type of evaluation techniques which may be performed utilizing thermal waves analysis is set forth in U.S. application Ser. No. 389,623, filed June 18, 1982, and now U.S. Pat. No. 4,513,384, issued Apr. 23, 1985. As set forth therein, where the thermal parameters of a layer of interest are known, a thermal wave analysis will provide information as to the thickness of that layer. Similarly, where the thickness of a layer is known, information concerning the thermal characteristics may be derived. The latter application also discloses a technique for assigning hypothetical thicknesses to the surface of a sample in order to perform depth profiling of thermal characteristics. However, it should be clear that the limitations inherent in such a thermal wave analysis of thin films are analogous to the limitations in electrical analysis of metallic films or an optical analysis of dielectric films. More specifically, either the thickness of a layer must be known to determine the character and identity of the material defining the layer or the material must be known in order to calculate the thickness of the layer. Clearly, it would be desirable if a system was available which could provide information on both the thickness and the material characteristics of the layer or thin film being tested.

Accordingly, it is an object of the subject invention to provide a new and improved method and apparatus which permits the evaluation of both thickness and compositional variables in a layered or thin film sample.

It is another object of the subject invention to provide a new and improved method and apparatus which permits the evaluation of both thickness and compositional variables in a layered or thin film sample through the use of two independent thermal wave detection systems.

It is still another object of the subject invention to provide a new and improved method and apparatus wherein temperature variations at the surface and within the sample are detected by two independent techniques permitting the evaluation of both thickness and compositional variables in a layered or thin film sample.

It is still a further object of the subject invention to provide a new and improved apparatus wherein two independent measurements of thermal wave activity may be obtained, and wherein the detection systems share the same hardware.

SUMMARY OF THE INVENTION

In accordance with these and many other objects, the subject invention provides for a method and apparatus which is capable of evaluating both thickness and compositional variables in a layered or thin film sample. The cornerstone upon which the subject invention is based, is the discovery that thermal wave detection systems can be divided into two categories. In both categories, an evaluation is made of temperature variations in the sample. However, in each category an independent measurement of the temperature variations is obtained. In the first group of detection techniques, the output signals of the thermal wave activity are a function of the temperature at the surface of the sample. In the second group of detection techniques, the output signals of the thermal wave activity are a function of the integral of the temperature distribution below the surface of the sample.

The two independent measurements provide two sets of equations defining the sample with only two unknowns, namely thickness and thermal conductivity. Since the latter two parameters are the same for both equations for a given sample, these two equations can be readily solved for the two unknowns. Thus, by providing a means to measure thermal waves both as a function of the surface temperature and as a function of the integral of the temperature beneath the sample surface, an analysis can be made of a sample to determine both thickness of the layer and its thermal conductivity. The thermal conductivity, in turn, provides information about the composition or stoichiometry of the material.

In accordance with the subject invention, thermal waves are generated in a sample by inducing a localized periodic heating at the surface of the sample. A first means is provided for detecting thermal wave signals that are a function primarily of surface temperature. A second detection means is provided which generates an output signal that is primarily a function of the integral of the temperature beneath the sample surface. Finally, a means is provided for processing the output signals from the two different types of detection means to derive information about layer thickness and compositional variables.

The two thermal wave detection systems discussed above (thermoacoustic microscopy and measurement of angular surface changes), both fall into the second category of techniques, namely, the measurement of thermal wave signals that are a function primarily of the integral of the temperature beneath the sample. Another system which could potentially be used to measure the integral of the temperature beneath the sample surface would be an interferometry technique. Such an interferometry technique is described in "Photo Displacement Imaging", Ameri et al, Photoacoustic Spectroscopy Meeting, *Technical Digest*, Paper THA6-1 Optical Society of America, 1981. However, at the present time, no interferometry technique exists which can detect signals at the high frequencies usually needed in thermal wave analysis of microelectronic elements.

Unfortunately, a similar situation has existed in the prior art with regard to detection techniques capable of measuring thermal wave signals that are a function primarily of the surface temperature. More specifically, none of the techniques which rely on measurement of surface temperature are capable of operating at the high frequencies necessary to deal with the very small features and the very thin films found in integrated circuits. Examples of such prior art techniques which cannot be used because of their inability to detect high frequencies include, for example, gas microphone photoacoustics. In this technique, a sample is placed inside a closed chamber containing air and a sensitive microphone. Periodic conduction of heat from the sample surface to the air in the chamber gives rise to periodic pressure changes in the chamber. These periodic pressure changes can be detected by the microphone. However, these systems have not been designed to detect pressure changes in the 0.1–20 MHz range and are therefore generally unsuitable for microelectronic applications. (See, for example, "Scanning Photo-Acoustic Microscopy (SPAM)", Wong, Scanned Image Microscopy, *Academic Press,* London, 1980.)

Another method for measuring temperature changes that are a function of the surface temperature of the sample include the monitoring of a laser which traverses a gas or liquid medium that is in contact with the heated area on the sample surface. The laser beam will undergo periodic deflections because of the periodic heat flow from the sample to the adjacent medium. (See, for example, "The Mirage Effect in Photothermal Imaging", Fournier and Boccara, Scanned Image Microscopy, *Academic Press*, London, 1980). A third technique for measuring surface temperatures utilizes an infrared detector that senses the periodic infrared emissions from the heated area on the surface of the sample. (See "Photoacoustic Microscopy at Low Modulation Frequencies", Luukkala, Scanned Image Microscopy, *Academic Press*, London, 1980). Similar to the photoacoustic technique, the latter measurement systems, while capable of measuring signals which are a function of the surface temperature, are not sufficiently sensitive to operate at the higher frequencies often required in integrated circuit applications.

This shortcoming has been solved through the development of an entirely new and unique thermal wave detection system. This new detection system measures thermal waves signals which are a function of the surface temperature and is capable of operating at the frequencies necessary to perform thermal wave analysis of the very small features and very thin films found in integrated circuits. This new and improved thermal wave detection system is the subject of U.S. Pat. application Ser. No. 612,075, and now U.S. Pat. No. 4,579,463, filed simultaneously herewith and incorporated by reference. The latter application sets out in detail the theory and operation of a detection system which satisfies the foregoing criteria. This detection system will be described briefly herein.

The new method and apparatus for detecting thermal waves in a sample is based on a principle that changes in optical reflectivity of a sample, occurring as it is periodically heated, will vary depending on the thermal characteristics of the sample. It has been known that optical reflectivity is dependent, to some extent, on temperature. This dependence is defined by the following equation:

$$R_T = R_o + (\delta R/\delta T)(\Delta T) \quad (2)$$

In this equation, $R_o$ represents the reflectivity at a set temperature and the second term in the equation gives the change of reflectivity resulting from the change in surface temperature. The term $(\delta R/\delta T)$ is the temperature coefficient of reflectivity which represents the rate of change in reflectivity with respect to the change in temperature. The term $\Delta T$ is the changing temperature at the sample surface.

Because of the inherent noise problems present in most measurement systems, it is quite difficult to detect information about the second term of the equation since the first term, $R_o$, is so much greater in magnitude. This difficulty is overcome by modulating the heating source. By this arrangement, periodic changes in reflectivity which are occurring at the frequency of the modulation beam can then be monitored. This information is processed by passing the signal through narrow bandwidth filters. The result is that only the periodic reflectivity signal $\Delta R_T$, as a result of the periodic surface temperature variations ΔT, is measured, rather than the absolute reflectivity $R_T$.

The periodic reflectivity signal $\Delta R_T$ is defined by the following equation:

$$\Delta R_t = (\delta R/\delta T)(\Delta T) \quad (3)$$

As seen from the above equation, the periodic reflectivity signal $\Delta R_T$ is dependent upon and thus provides a measure of the periodic surface temperature ΔT. The periodic surface temperature, in turn, provides information about thermal wave propagation and interaction in the material. Thus, with suitable mathematical equations, one can determine the thermal wave activity based on the measured changes in reflectivity. Calculation of the thermal waves is carried out by normalizing the signals against a known reference sample, as discussed in greater detail below.

Based on the foregoing, it is another aspect of the subject invention to provide an apparatus having a first detection system based on reflectivity measurements and a second detection system based on any one of the known high frequency measurement techniques which generate an output signal that is a function of the integral of the temperature beneath the surface of the sample. As stated above, suitable techniques for performing the latter measurements include the detection of acoustic waves as in thermoacoustic microscopy or the monitoring of angular surface changes of the sample through the measurement of the angular displacements of the reflected probe beam off the sample.

It is still a further object of the subject invention to provide a method and apparatus which advantageously combines the two independent detection techniques in a manner such that identical hardware may be utilized to achieve the desired result at virtually no extra cost. As will be discussed in detail below, the hardware associated with the measurement of thermal waves by the deflection technique and by the reflectivity technique are virtually identical. In the preferred embodiment, the only difference between the two detection systems is the means for processing the output signals.

As discussed in detail below, the subject invention includes a radiation probe which is directed on a portion of the sample surface which has been subjected to a periodic localized heating. A first detection means is provided for measuring the intensity variations of the reflected radiation probe which results from the periodic changes in reflectivity of the sample due to the periodic heating. In addition, a second detection means is provided for measuring the angular displacements of the reflected radiation probe also resulting from the periodic heating. A means is provided for processing the output signals from both the detection means such that information about both layer thickness and compositional variables may be evaluated.

In the preferred embodiment, the first and second detector means can be defined by a single photodetector element, such as a split-cell detector. As discussed below and in U.S. Pat. No. 4,521,118, the deflection of a probe beam can be calculated by comparing the difference between the output signals of both halves of a split-cell photodetector. In accordance with the subject invention, the output signals from the two halves may also be summed to give an absolute indication of the intensity variations of the beam. Thus, by taking either the difference or the sum of the output signals of a split detector, both the amount of deflection and the intensity variations of a reflected probe beam, based on the periodic heating of the sample, can be measured.

Further objects and advantages of the subject invention will become apparent from the following detailed description taken in conjunction with the drawings in which:

BEST MODES FOR CARRYING OUT THE INVENTION

Figure 2:
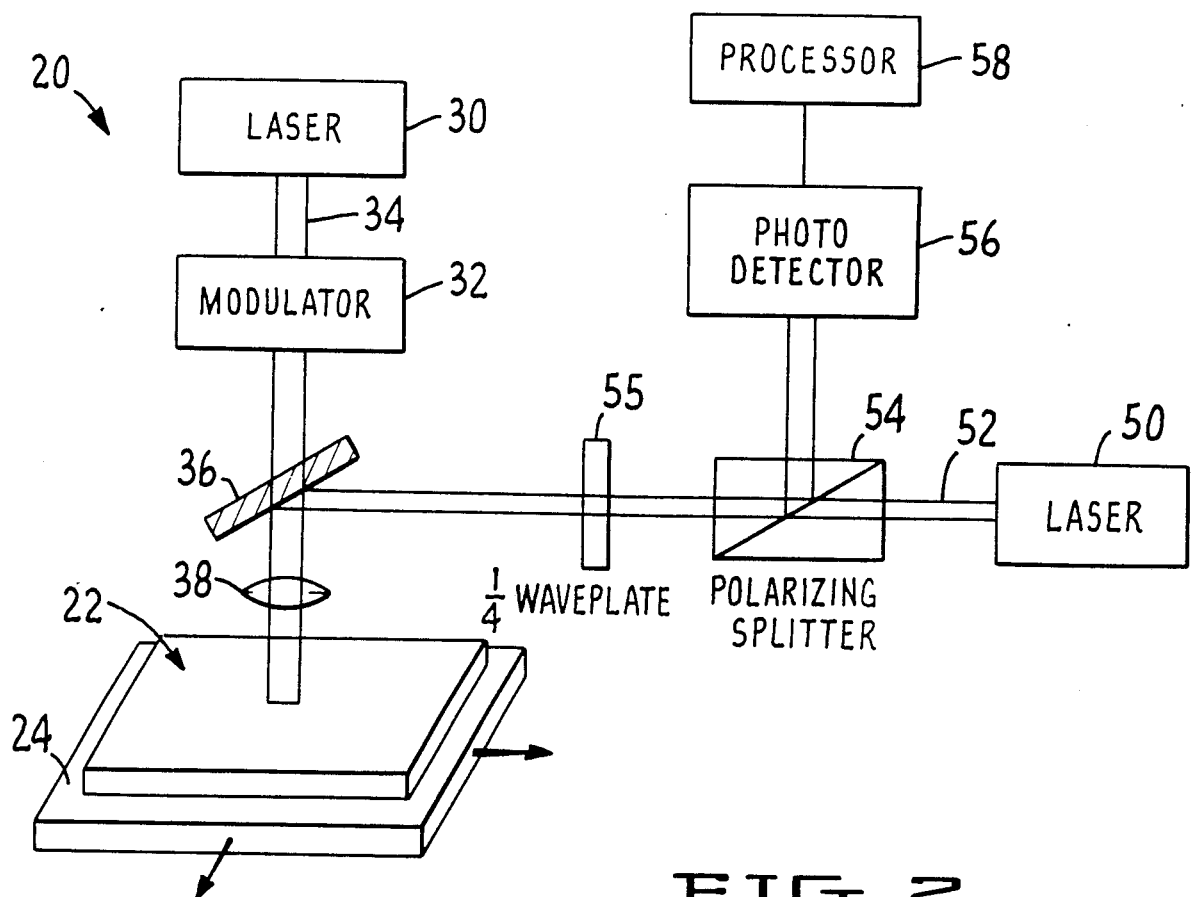
FIG. 2 is a composite block and schematic diagram of the apparatus of the subject invention, capable of evaluating both thickness and compositional variables in a sample.

Referring to FIG. 2, there is illustrated an apparatus 20 for carrying out the method of the subject invention. The subject apparatus is arranged to provide two independent means for detecting thermal wave signals utilizing essentially the same hardware. It is to be understood that the scope of the subject invention is considerably broader than the embodiment shown in FIG. 2, however, the arrangement illustrated therein is considered to be uniquely suited for carrying out the subject method in the least expensive and efficient manner.

As set forth above, the subject invention is capable of evaluating both thickness and compositional variables in a sample 22 by studying thermal waves generated in a sample. In FIG. 2, sample 22 is shown resting on a platform 24. Platform 24 is capable of movement in two orthogonal directions in a manner such that the sample can be rastered with respect to the heating and probe beams of the subject invention if mapping or imaging is desired. Controllable stages are well known in the art and also disclosed in U.S. Pat. No. 4,255,971 cited above.

In accordance with the subject invention, a means must be provided for generating thermal waves. In the illustrated embodiment, this means is defined by a laser 30 which is intensity modulated by modulator 32. Preferable, the laser beam 34 is focused on the surface of the sample 22 by a microscopic objective 38. While it is not necessary to focus the modulated heating beam, in some situations it may be desirable to do so to improve spatial resolution. Beam 34 is intended to create a periodic surface heating in the sample. This periodic heating is the source of thermal waves that propagate outwardly from the center of the beam. The thermal waves reflect and scatter as they interact with thermal features in the sample, such as the interface between a thin film and a substrate, thereby changing the temperatures on the surface and within the sample.

The intensity modulated heating source could be supplied by electromagnetic radiation at various wavelengths, including X-Rays, gamma rays, infrared, ultraviolet, visible light, microwaves or radio frequencies. The intensity modulated source can also be generated through thermal excitation arising from the interaction of the sample with an intensity modulated stream of particles, such as a beam of electrons, protons, neutrons, ions or molecules. However, because of the ease of directing and focusing a laser beam, and because of the concurrent use of a laser probe, it is preferable that the periodic heating source be provided by an intensity modulated laser.

The intensity modulated beam 34 is passed through dichroic mirror 36 prior to passing through the microscopic objective 38. In the preferred embodiment, the heating beam is an argon ion laser and the dichroic mirror is transparent to argon ion radiation. As will be discussed below, the dichroic mirror functions to reflect the probe laser beam, which is preferably generated by a helium-neon laser.

In accordance with the subject invention, two independent systems are provided for detecting thermal waves. The first system is of the type which generates output signals that are a function primarily of the surface temperature. The second system for detecting thermal waves should be of the type which generates output signals that are primarily a function of the integral of the temperature beneath the sample surface.

Two known thermal wave detection systems which satisfy the latter criteria were discussed above. More particularly, a thermoacoustic detection system, of the type described in U.S. Pat. No. 4,255,971, cited above, functions to produce output signals which are a function of the integral of the temperature beneath the sample surface. Therefore, such a thermoacoustic technique, utilizing a piezoelectric transducer connected to the sample would be operative to function as the second detection means in the method and apparatus of the subject invention. However, because the thermoacoustic system is a "contact technique", it is less desirable, particularly in integrated circuit applications.

Accordingly, in the preferred embodiment of the subject invention, the second detection means is defined by a laser probe of the type disclosed in U.S. Pat. Nos. 4,521,118 and 4,522,510, cited above. In this technique, thermal waves signals are detected by monitoring the local angular changes occurring within the heated area on the surface of the sample. More specifically, when thermal waves are generated in a localized region of the sample, the surface of the sample undergoes periodic angular changes within the periodically heated area. To monitor these changes, a laser beam is focused on the surface of the sample at some distance from the center of the heated area in a manner such that it is reflected from the surface. Because of the local angular changes occurring at the surface of the sample, the reflected off-center probe beam will experience angular displacements in a periodic fashion. By measuring the angular displacements of this probe beam, information about the thermal wave activity in the sample can be determined.

The latter thermal wave detection technique generates output signals that are primarily a function of the integral of the temperature beneath the sample surface. As will be discussed immediately below, the components for implementing such a thermal wave detection technique are virtually identical to the components necessary for implementing the reflectivity detection technique.

In order to carry out the object of the subject invention, a thermal wave detection system must also be provided which generates output signals that are a function primarily of the surface temperature. As pointed out above, in the prior art, there are a few measurement techniques which function to measure surface temperatures. These include, for example, infrared measurements and photoacoustic technology. However, none of the known prior art measurement systems operate at the frequencies needed for applications with microelectronic samples. More specifically, in order to detect micron sized features in a sample, or to measure submicron thick thin films, it is necessary to modulate the heating beam in the frequency range from 0.1–20 MHz. To date, none of the prior art methods which detect surface temperatures have enough sensitivity to operate at these high frequencies.

This difficulty is overcome, however, in the subject invention by utilizing an entirely new thermal wave detection technique which is based on reflectivity. This new detection system is described in detail in copending application, Ser. No. 612,075 and now U.S. Pat. No. 4,579,463, cited above. As set forth therein, thermal wave activity can be detected by monitoring the periodic changes in reflectivity at the surface of the sample within the periodically heated area.

The periodic changes in reflectivity can be monitored by impinging a probe beam on the surface of the sample and recording the intensity variations of the reflected beam. As the probe beam is reflected off the surface of the sample, it interacts with the electrons and thus with lattice structure of the sample at its surface. The lattice structure of the sample will undergo periodic changes as the temperature of the sample changes periodically. The probe beam essentially "sees" the changes of this lattice structure at the sample surface and the level of intensity of the beam changes along with the changes in thermal conditions at the sample surface. Based on the above, it can be seen that both the deflection type measurement system and the reflectivity technique are both based on monitoring a radiation probe beam which has been reflected off the surface of the sample within the periodically heated area. The latter situation permits the construction of an apparatus wherein only one set of components is utilized while permitting two independent measurements to be taken.

Referring again to FIG. 2, the first and second detection means of the subject invention are illustrated. More specifically, the light probe of the detection systems is generated by a helium-neon laser 50. Other sources of electromagnetic radiation may be used for the probe beam as long as the beam is reflected in accordance with Snell's law and its reflectivity is affected by the temperature changes on the sample surface in a measurable manner.

Probe beam 52, emanating from helium-neon laser 50, is then passed through a polarizing splitter 54. The polarizing splitter is oriented in a manner such as to let the coherent light emanating from laser 50 to pass freely therethrough. This splitter will, however, deflect all light whose phase has been rotated through 90° relative to beam 52. The reason for this arrangement will become apparent below.

Light probe 52 is then passed through a $\frac{1}{8}\lambda$-waveplate 55. Waveplate 55 functions to rotate the phase of the probe beam by 45°. As can be appreciated, on the return path of the beam, waveplate 55 will rotate the phase of the beam another 45° so that when it reaches splitter 54, the phase of the beam will have been rotated a total of 90° from the incoming orientation. By this arrangement, the splitter 54 will deflect the retro-reflected light beam up to detector 56, as discussed in more detail below.

After the probe beam 52 initially passes through waveplate 55, it is reflected downwardly by dichroic mirror 36. As pointed out above, the dichroic mirror is transparent to argon ion light, but will reflect the light rays in the helium-neon frequencies. The optical system, including the dichroic mirror 36 and microscope objective 38, are adjustable to permit the focusing of the probe beam with respect to the heating beam. As discussed above, microscope objective 38 is desirable where high spatial resolution is needed. However, it is only necessary for the probe beam to be directed within a portion of the periodically heated area.

As can be appreciated, when the heating beam is directed on the surface of the sample, thermal waves will project radially outwardly therefrom for a distance of one or two thermal diffusion lengths. This generally circular area of periodic heating has a diameter D which can be calculated. More specifically, the diameter D of this circular periodically heated area is equivalent to $$D = 2 \sqrt{(\text{spot radius } r_o)^2 + (\text{thermal diffusion length})^2} \quad (4)$$

In the above equation, the spot radius $r_o$ is the radius of the modulated heating beam 34. The thermal diffusion length is the distance which the thermal waves will travel in the sample and is related to the thermal constants of the sample and the modulution frequency of the heating beam.

Theoretically, the subject apparatus will operate as long as the probe beam is directed within this heated area. However, the signals of interest are extremely small and therefore it is desirable to make efforts to maximize the detectable signal. For example, the angular surface changes which the sample undergoes as a result of the thermal waves, are at most, $10^{-4}$ radians. Similarly, the periodic changes in reflectivity at the surface of the sample are only $10^{-5}$ of the DC level of the probe beam.

Figure 3:
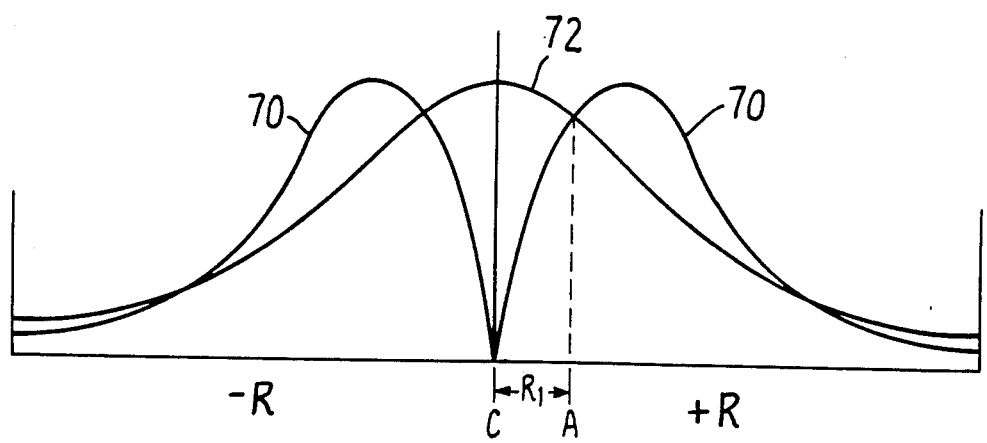
FIG. 3 is a graphical representation comparing signal strength available in both reflectivity and deflection-type thermal wave detection systems, measured as a function of the distance on the sample surface from the heating source.

A graphical representation of the signal strength available for detection by the two measurement techniques, as a function of the distance on the sample surface from the heating source, is illustrated in FIG. 3. In that figure, the horizontal axis indicates the distance away from the central heating point C on the surface of the sample. The vertical axis is a measure of available signal strength. Curve 70 represents signals available in the deflection detection technique, while curve 72 illustrates the signal strength available when measuring changes in reflectivity.

As illustrated in FIG. 3, the reflectivity signals 72 of interest are maximized at the center of the heating beam. The signals then taper off as the distance from the heating beam increases. This relationship can be intuitively understood since the maximum periodic heating will occur at the center of the heating beam and, therefore, the maximum changes of reflectivity will be coincident therewith. Accordingly, to maximize the signal output when measuring for reflectivity, the probe beam can be aligned to be coincident with the heating beam 34. However, in order to facilitate measurement by both detection systems, the optimum location of the probe beam may be different.

Curve 70, corresponding to the deflection technique, indicates that there are virtually no signals available at the center of the heating beam. The signals then increase at positions located radially outwardly from the center of the heating beam and finally taper off towards the border of the periodically heated area. This signal pattern is based on the fact that at the center of the heating beam, the surface of the sample is undergoing vertical displacements only. The angular surface displacements of interest occur away from the center of the heating beam. Of course, as the distance from the heating beam 34 further increases, the deflection signals will also taper off. Accordingly, thermal wave detection in the deflection measurement system can be maximized at a point offset from the center of the beam.

As discussed in U.S. Pat. No. 4,521,118, cited above, it is also desirable in the deflection measurement system to focus the probe beam in only one-half of the heated area. This arrangement is preferable because the two halves of the heated area will produce complementary and cancelling angular displacement effects in the probe beam. Therefore, in the preferred arrangement, when measuring the angular surface changes of the sample, the beam should be directed within one-half of the periodically heated area, spaced from the heating beam. In a typical configuration, using a modulation frequency of 0.1 to 20 MHz and a silicon substrate, the spacing between the heating beam and the probe beam should be on the order of 1 micron when the heating beam spot size is on the order of 1 micron.

When carrying out the method of the subject invention, two approaches may be implemented. If maximum signal strength is desired, the optics defined by mirror 36 and objective 38 should be adjusted to focus the probe beam 52 at different locations during each different measurement. For example, during the measurement of the changing reflectivity signals, the probe beam should be focused coincident with the heating beam. In contrast, during measurement of the angular surface displacements, the probe beam should be focused at a point one to two microns away from the center of the heating beam. While the latter approach will provide for maximum signal strength, it is of course, slightly more complicated.

In a simpler approach, which is suitable in a situation where signal strength is less critical, the probe beam can be focused at a point in between the maxima of the two signals. As illustrated in FIG. 3, if the beam is focused at a point A, at distance $R_1$, from the center of the heating beam and between the maxima of the two signals of interest, fairly strong signals can be obtained for both detection systems. At this focus point, the processor can be arranged to analyze the signals both for periodic reflectivity changes in the sample and for angular surface changes. These measurements can be done in succession, as discussed more fully hereinbelow.

After the probe beam is reflected off the surface of the sample, it again passes up to dichroic mirror 36 where it is, in turn, redirected along the incoming beam path and through the $\frac{1}{8}\lambda$-waveplate 55. As discussed above, waveplate 55 rotates the phase of the probe beam by another 45° such that when the beam reaches splitter 54, its phase has been rotated 90° with respect to the original beam. Accordingly, the splitter will deflect the retro-reflected probe beam upwardly towards photodetector 56.

In accordance with the subject invention, a detector means must be provided which can monitor the deflections of the probe beam due to the changing angular surface conditions of the sample. In addition, a detection means must be provided for monitoring the intensity variations of the probe beam occurring as a result of the periodic reflectivity, changes at the surface of the sample. The latter criteria, namely, measurement of intensity changes, could be satisfied by a standard photodetector.

Figure 1:
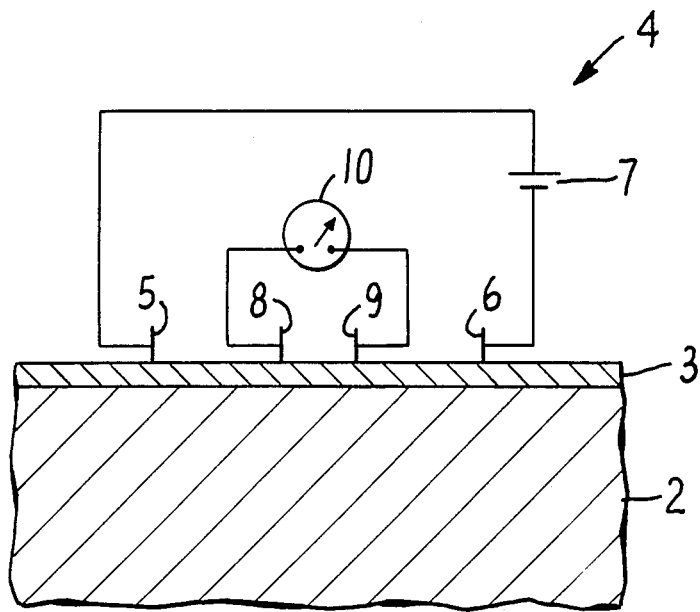
FIG. 1 is a combination block and schematic diagram of a four-point probe electrical detection system found in the prior art.
Figure 4:
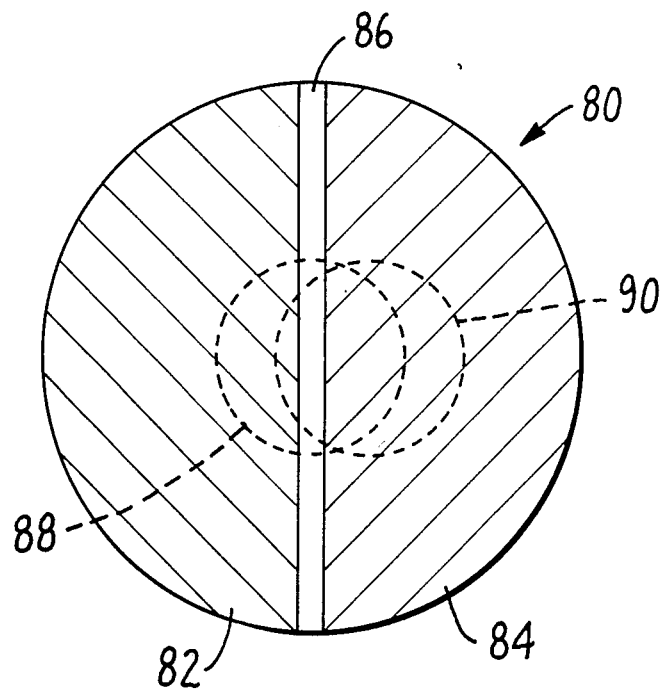
FIG. 4 is a bottom plan view of a typical split-cell photodetector of the type which may be utilized in the subject invention.

There are a number of detectors which are capable of satisfying the former criteria, namely monitoring deflections of a laser beam. For example, a photodetector having a knife-edged beam stop over one-half of the detector could be used to determine intensity variations as the beam was deflected through angular displacements. The latter type of detector, however, is a bit primitive and has certain drawbacks. Accordingly, it would be preferable to utilize one of the more recently developed "split" detectors. Referring to FIG. 4, one form of a split detector is shown. Split detector 80 is defined by a photodetector having two sensing elements 82 and 84 located in a side-by-side arrangement separated by a divider 86 only a few microns thick. Each sensing element generates an electrical signal based on the intensity of the light reaching that sector. Before the modulated heating is applied, the probe beam will be centered on the split detector, such that each sector receives equal amounts of optical radiation. By comparing the output of the two sensing elements during the modulated heating, variations due to the angular displacement of the beam can be determined.

The advantage of using a split cell detector is that any other signals, including those resulting from changes of reflectivity of the beam, will affect both sides of the detector equally. Accordingly, comparison of the output of both sensing elements will result in elimination of any signals beyond the effects of the beam displacement. This type of detector is also advantageous in that it tends to cancel any noise effects from the beam itself. A discussion of split detectors and their attributes can be found in "Noncontact Optical Position Sensing Using Silicon Photodetectors" by William Light, Apr. 1982. As used herein, the term "split detector" is intended to mean a photodetector having more than one sensing element. Accordingly, multi-element photodetectors, such as quadrant detectors which have four or more segments are also suitable for use in the subject invention.

The operation of the split cell 80, when being utilized to measure angular displacements in the probe beam will be briefly discussed. As pointed out above, the split cell is designed such that each half 82 and 84 will generate a current proportional to the amount of light striking that segment. Accordingly, when the probe beam is centered on the photodetector, as illustrated by the phantom line circle 88, equal amounts of light will strike each half of the cell and the output signals generated by each segment will be equal. In operation, the processor functions to take the difference between the two signals to calculate the displacement of the beam. When the probe beam is centered, as indicated by circle 88, the two signals are equal, such that the difference will be zero, indicating that there is no displacement of the beam. If the beam should be shifted off the center, as indicated by phantom circle 90, more light will fall on one half of the split cell than the other. The difference between the currents generated by the two segments gives a measure of the amount of the deflection of the beam. Thus, a split cell detector provides a simple method of monitoring the angular displacements of the probe beam.

The same split cell 80 can also be used to monitor the reflectivity changes of the probe beam. As set forth above, each half of the photocell will put out a current signal proportional to the amount of light hitting the surface. Thus, the sum of the signals of both segments gives a measure of the absolute value of the light energy falling on the photodetector. As the beam changes in intensity due to the change in periodic reflectivity at the surface of the sample, the total output signals of the photodetector will change in proportion. This result is true even if the beam is experiencing angular displacements due to the angular changes on the surface of the sample. Stated differently, even if the beam is located off center of the photocell, the sum of the two sides will still give a value of the total of the energy reaching the surface of the photodetector.

By analogy, the output of detector 80 (when measuring changes in reflectivity of the sample), will also be unaffected by the small changes in the diameter of the probe beam which may be induced by the periodic heating. As described in applicants' prior U.S. Pat. No. 4,522,510, issued June 11, 1985, periodic heating of a sample can create a periodically changing thermal lens in the sample. The presence of the thermal lens can be monitored by using a probe beam. For example, if a probe beam is passed, off-axis, through a periodically changing thermal lens, the beam will be periodically deflected. If the probe beam is passed through the center of thermal lens, its diameter will vary periodically by a small amount. The latter effect is described in U.S. Pat. No. 4,243,327, issued Jan. 6, 1981, to Frosch.

The patent to Frosch describes a method for detecting the changes in diameter of a reflected probe beam induced by a changing thermal lens. This method is based on the principle that as the probe beam varies in diameter, the number of photons striking a fixed area having a diameter that is smaller than the probe beam diameter, will vary over time. Thus, the detector in Frosch is designed to measure the number of photons striking a particular area over time, that is, the areal density of the photons at the detector surface.

In contrast, and as discussed above, in the subject device, the detector 56(80), in combination with processor 58, is arranged to measure the total amount of photons reflected from the sample, without regard to the location at which the photons impact on the detector or the areal density of those photons at the detector surface. In fact, since the output of detector 56 is proportional to the number of photons reflected from the sample surface, the resulting signals will be unaffected by the small changes in the beam diameter which may be induced by the periodic heating. Thus, in the subject device, the measurement of intensity changes of the reflected probe beam due to changes in reflectivity of the sample is independent of relatively small changes in both the position of the beam on the detector, as well as the diameter of the beam.

As pointed out above, detector 56(80) is arranged so that the total amount of power in the reflected probe beam is measured. This measurement could not be accomplished if any portion of the probe beam moved off the surface of the detector. As can be appreciated, if part of the probe beam misses the detector surface, the output signals therefrom would not be proportional to the total number of photons in the reflected probe beam. Therefore, it is necessary that the apparatus be arranged such that the diameter of the probe beam underfills, or is less than, the active surface of the photodetector (i.e. falls within its boundary), as shown in FIG. 4.

In summary, a split cell may be used to monitor both angular displacements of the probe beam and changes in intensity. The former can be monitored by taking the difference between the output signal of the two halves of the detector while the intensity variations can be monitored by taking the sum of the two halves. Thus, simply by altering the way in which the output signals from the split photodetector are processed, information about either the deflection or change in intensity of the probe beam can be derived. By this arrangement, in the preferred embodiment of the subject invention, the detection means can be defined by a single photodetector element.

The output signals from photodetector 56 are supplied to a processor 58. As set forth above, depending upon the measurements being taken, the processor will either be summing or subtracting the signals emanating from photodetector 56. Obviously, this process can be switched back and forth quickly if the sample is rastered beneath the heating and probe beams as would be the case where mapping or imaging of features is desired.

Processor 58 is also designed to perform a thermal wave analysis on the sample. The operation of processor 58 is dependent on the type of testing configuration which is utilized. The derivation of thermal wave signals from the measurement of beam displacements or changes in intensity are carried out by normalizing either the phase or magnitude of the measured signals. These normalized values are then compared to normalized values taken from a known reference sample. Calculations of this general type are discussed in "Thermal Wave Depth Profiling: Theory" by Jon Opsal and Allan Rosencwaig, *Journal of Applied Physics*, June 1982. The calculations set forth in the latter article are based on the detection techniques which measure an output signal that is a function of the integral of the temperature beneath the sample surface. As discussed above, the reflectivity measurement system produces an output signal that is primarily a function of the surface temperature and therefore the calculations must be modified accordingly. In specific manufacturing situations, it may be possible to forego the steps of normalizing the signals against a model. More specifically, in an inline manufacturing situation, where most of the parameters are known, simple point testing with comparison of output signals to an expected signal may be sufficient.

In any case, processor 58 is designed to generate independent output information based on the two measurement techniques provided in the subject apparatus. Having two independent measurements, permits an analysis of the sample which has heretofore been impossible. As discussed above, in the prior art measurement techniques, it was not possible to perform an analysis if both the thickness of the layer of interest and its electrical or thermal parameters were unknown. Thus, in order to calculate compositional variables, it was necessary to know the thickness of the layer of interest. Conversely, to calculate the thickness of the layer of interest, it was necessary to know the nature of the material.

This roadblock has been completely overcome in the subject invention because of the availability of two independent output signals. Two independent measurements provide two sets of equations, each having two unknowns, (thickness and thermal conductivity). The latter parameters are, of course, the same for both equations for a given sample. Thus, these two equations can be solved for the two unknowns.

Examples of these type of equations can be found in "Thermal Wave Detection and Thin Film Thickness Measurements with Laser Beam Deflection", Opsal et al, *APPLIED OPTICS*, Vol. 22; No. 20 Oct. 15, 1983. At page 3172 of that article, equations are set forth for output signals that are primarily a function of the surface temperature as well as output signals that are a function of the integral of the temperature beneath the sample surface. Accordingly, it is now possible to obtain complete information about the thickness of a layer of interest and the thermal variables such as the thermal conductivity of the system. From the thermal conductivity, information can be derived about the sample's composition or its stoichiometry. Furthermore, where the sample is a metal, mathematical transformations are available to permit the derivation of information about electrical conductivity of the sample as well.

In summary, there has been disclosed a new and improved method and apparatus for determining both thickness and compositional variables in a material. The apparatus includes two detection means measuring thermal wave signals in the sample that are generated by a periodic localized heating. One detection system is of the type which generates output signals that are a function primarily of the surface temperature. The second detection means is a type which generates output signals that are primarily a function of the integral of temperature beneath the surface. A means is provided for processing these two independent measurements, and for calculating the two unknowns, namely, layer thickness and compositional variables in the sample. A preferred embodiment is disclosed wherein the two detection means may be implemented in an apparatus with a single set of probe elements.

While the subject invention has been described with reference to a preferred embodiment, various other changes and modifications could be made therein by one skilled in the art, without varying from the scope and spirit of the subject invention as defined by the appended claims.

We claim:

1. Apparatus for evaluating thickness and compositional variables in a layered or thin film sample by analyzing thermal waves in a sample, said thermal waves being generated by a periodic localized heating at a spot on the surface of the sample, said apparatus comprising:

first means for detecting thermal waves, said first means being of the type which generates output signals that are a function primarily of the surface temperature said first means including a probe for emitting a beam of radiation;

a means for directing the radiation probe beam within a portion of the periodically heated area on the sample surface in a manner such that the radiation probe beam reflects off the surface of the sample; and a means for measuring the intensity variations of the reflected radiation probe beam resulting from the periodic changes in optical reflectivity induced by the periodic heating with the measured intensity variations being independent of changes in beam diameter and position;

second means for detecting thermal waves, said second means being of the type which generates output signals that are primarily a function of the integral of the temperature beneath the sample surface; and means for processing the output signals from said first and second detection means such that information about both layer thickness and compositional variables of the sample may be evaluated.

2. An apparatus as recited in claim 1 wherein said second detection means is defined by a means for monitoring the angular changes of the sample surface within the area which has been periodically heated.

3. An apparatus as recited in claim 2 wherein said second detection means comprises:

a probe for emitting a beam of radiation;

means for directing said radiation probe beam within a portion of the periodically heated area on the sample surface in a manner such that said radiation probe beam reflects off the surface of the sample; and means for measuring the angular displacement of the reflected probe, said displacement resulting from the local angular changes in the surface conditions of the sample.

4. An apparatus as recited in claim 3 wherein said means for directing the radiation probe beam of said second detection means is arranged such that during the measurement of the angular displacements of the radiation probe beam, the radiation probe beam is directed on one-half of the periodically heated area on the surface of the sample and spaced from the center of the periodically heated area and during the measurement of reflectivity changes, the radiation probe beam is directed at the center of the periodically heated area.

5. An apparatus as recited in claim 3 wherein the measuring means of both the first and second detection means includes a single photodetector capable of measuring both the angular displacements and the intensity variations of the reflected probe beam.

6. An apparatus as recited in claim 5 wherein said apparatus is arranged such that the probe beam underfills the surface of said photodetector.

7. An apparatus as recited in claim 1, wherein said means for measuring the intensity variations of the reflected radiation probe beam is defined by a photodetector with said apparatus being arranged so that the probe beam underfills the surface of said photodetector.

8. A method for evaluating the thickness and compositional variables in a layered or thin film sample by analyzing thermal waves present in the sample, said thermal waves being generated by a periodic localized heating at the surface of the sample, said method comprising the steps of:

A. detecting thermal wave signals within the periodically heated area on the surface of the sample that are a function primarily of the surface temperature, said detecting step being performed by directing a radiation probe beam within a portion of the periodically heated area on the surface of the sample in a manner such that the radiation probe beam reflects off the surface of the sample; and measuring the intensity variations of the reflected radiation probe beam resulting from the changes in optical reflectivity of the sample induced by said periodic heating with the measured variations being independent of changes of beam diameter and position;

B. detecting thermal wave signals within the periodically heated area on the surface of the sample that are primarily a function of the integral of the temperature beneath the sample; and C. processing the measured thermal wave signals such that information about both layer thickness and compositional variables may be evaluated.

9. A method as recited in claim 8 wherein the step of detecting thermal wave signals recited in Step B is performed by measuring the periodic angular changes of the sample surface within the area which has been periodically heated.

10. A method as recited in claim 9 wherein said step of monitoring the periodic angular changes of the sample surface comprises the following steps:

focusing a radiation probe beam within a portion of the periodically heated area on the sample surface such that the radiation probe beam reflects off the surface of the sample; and measuring the angular displacements of the reflected probe beam, said displacements resulting from the local angular changes in the surface conditions of the sample.

11. An apparatus for evaluating thickness and compositional variables in a layered or thin film sample by analyzing thermal waves present in the sample, said thermal waves being generated by a periodic localized heating at the surface of the sample, said apparatus comprising:

a probe for emitting a radiation beam;

means for directing the radiation probe beam within a portion of the periodically heated area on the sample surface in a manner such that the radiation probe beam reflects off the sample surface;

first means for measuring the intensity variations of the reflected radiation probe beam resulting from changes in optical reflectivity of the sample induced by the periodic heating with the measured intensity variations being independent of changes in beam diameter and position, wherein said first means functions to generate output signals that are primarily a function of the surface temperature of the sample;

second means for measuring the angular displacements of the reflected radiation probe beam resulting from angular deviations of the sample surface induced by the periodic heating and generating output signals that are primarily a function of the integral of the temperature beneath the sample surface; and means for processing the output signals from said first and second measuring means such that information about both layer thickness and compositional variables of the sample may be evaluated.

12. An apparatus as recited in claim 11 wherein said first and second measuring means are defined by a single photodetector.

13. An apparatus as recited in claim 12 wherein said means for directing the radiation probe beam of said second detection means is arranged such that during the measurement of the angular displacements of the radiation probe beam, the radiation probe beam is directed on one-half of the periodically heated area on the surface of the sample and spaced from the center of the periodically heated area and during the measurement of reflectivity changes, the radiation probe beam is directed at the center of the periodically heated area.

14. An apparatus as recited in claim 12 wherein said apparatus is arranged such that the probe beam underfills the surface of the photodetector.

15. A method for evaluating thickness and compositional variables in a layered or thin film sample by analyzing thermal wave signals in the sample, said thermal waves being generated by a periodic localized heating at the surface of the sample, said method comprising the steps of:
- A. directing a radiation probe beam within a portion of the periodically heated area on the sample surface in a manner such that the radiation probe beam reflects off the sample surface;
- B. measuring the periodic intensity variations of the reflected radiation probe beam resulting from the changes in optical reflectivity of the sample induced by the periodic heating with the measured intensity variations being independent of beam diameter and position and generating output signals that are primarily a function of the surface temperature;
- C. measuring the periodic angular displacements of the reflected radiation probe beam resulting from angular deviations of the sample surface induced by the periodic heating and generating output signals that are primarily a function of the integral of the temperature beneath the sample; and
- D. processing the output signals measured in Steps B and C to derive information about both layer thickness and compositional variables of the sample.

16. A method as recited in claim 15 wherein during said step B of measuring the intensity variations of the reflected probe beam, the radiation probe beam is directed to be coincident with the center of the periodically heated area.

17. A method as recited in claim 15 wherein during the step of measuring the angular displacements of the reflected radiation probe beam, the radiation probe beam is directed on one-half of the periodically heated area and spaced from the center of the periodically heated area.